United States Patent
Dang et al.

(10) Patent No.: US 9,435,002 B2
(45) Date of Patent: Sep. 6, 2016

(54) CONTINUOUS PROCESSES FOR HYDROLYZING HEMICELLULOSES FROM LIGOCELLULOSIC MATERIALS WITH CLEANING SYSTEM

(71) Applicant: API Intellectual Property Holdings, LLC, Atlanta, GA (US)

(72) Inventors: Zheng Dang, Lilburn, GA (US); Mehmet Sefik Tunc, Thomaston, GA (US); Ziyu Wang, Newnan, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 14/714,214

(22) Filed: May 15, 2015

(65) Prior Publication Data

US 2015/0354019 A1    Dec. 10, 2015

Related U.S. Application Data

(60) Provisional application No. 62/009,211, filed on Jun. 7, 2014.

(51) Int. Cl.
 *C13K 13/00* (2006.01)
 *C07C 51/00* (2006.01)
 *C07D 307/50* (2006.01)
 *C13K 1/02* (2006.01)

(52) U.S. Cl.
 CPC ............. *C13K 13/002* (2013.01); *C07C 51/00* (2013.01); *C07D 307/50* (2013.01); *C13K 1/02* (2013.01); *C13K 13/00* (2013.01)

(58) Field of Classification Search
 CPC .................................................. C13K 13/002
 See application file for complete search history.

*Primary Examiner* — Golam M M Shameem
(74) *Attorney, Agent, or Firm* — Ryan P. O'Connor (57) ABSTRACT

A continuous process for producing hemicellulose sugars from a biomass extraction liquor is provided. A system is configured for continuously producing hemicellulose sugars and/or hemicellulose derivatives from a biomass extraction liquor, the system comprising at least a first hydrolysis reactor and a second hydrolysis reactor. Each of the hydrolysis reactors is in switchable communication with (i) an operating feed stream of a biomass extraction liquor containing water, hemicellulose oligomers, and dissolved or suspended lignin, and (ii) a cleaning feed stream of a cleaning agent selected from the group consisting of steam, an alkaline solution, an organic solvent, and combinations thereof. The cleaning agent dissolves precipitated lignin formed from the lignin under the hydrolysis reaction conditions.

22 Claims, 3 Drawing Sheets

FIG. 1

FIG. 2 lignin precipitate dissolved by 60% ethanol lignin precipitate dissolved by 2% NaOH lignin precipitate

FIG. 3

Table: Mono-sugars concentration of hemicellulose extract after acid hydrolysis at various combinations of temperature, acid (H$_2$SO$_4$) charge, and time.

| Acid charge on the top of the solution | 0.50% | 0.50% | 1.00% | 1.00% | 1.00% | 1.00% | 2.00% | 2.00% | 2.00% | 2.00% |
|---|---|---|---|---|---|---|---|---|---|---|
| Time, min | 30 | 15 | 90 | 30 | 15 | 8 | 30 | 10 | 8 | 6 |
| Temperature, °C | 150 | 160 | 120 | 140 | 150 | 160 | 120 | 140 | 150 | 160 |
| Glucose, g/l | 2.979 | 2.871 | 3.128 | 3.272 | 3.262 | 3.064 | 2.828 | 3.229 | 3.041 | 2.987 |
| Xylose, g/l | 11.054 | 10.661 | 10.989 | 11.648 | 12.398 | 11.925 | 10.619 | 11.859 | 11.959 | 11.610 |
| Galactose, g/l | 2.890 | 2.960 | 1.467 | 1.054 | 3.3 | 3.320 | 1.551 | 2.527 | 3.273 | 3.233 |
| Arabinose, g/l | 1.959 | 1.806 | 1.855 | 1.956 | 2.008 | 2.012 | 1.796 | 1.852 | 1.926 | 1.987 |
| Mannose, g/l | 1.762 | 1.278 | 1.413 | 1.616 | 1.6215 | 1.541 | 1.307 | 1.285 | 1.474 | 1.523 |
| Sum, g/l | 20.64 | 19.57 | 18.85 | 19.55 | 22.59 | 21.86 | 18.10 | 20.75 | 21.67 | 21.34 |

CONTINUOUS PROCESSES FOR HYDROLYZING HEMICELLULOSES FROM LIGOCELLULOSIC MATERIALS WITH CLEANING SYSTEM

PRIORITY DATA

This patent application is a non-provisional application claiming priority to U.S. Provisional Patent App. No. 62/009,211, filed Jun. 7, 2014, which is hereby incorporated by reference herein.

FIELD OF THE INVENTION

The present invention generally relates to improved processes for recovering fermentable hemicellulosic sugars from lignocellulosic biomass.

BACKGROUND OF THE INVENTION

Biomass refining (or biorefining), which separates cellulose, hemicellulose, and lignin from biomass feedstocks, is becoming more prevalent in industrial plants. Cellulose fibers and sugars, and hemicellulose sugars, are being used by many companies for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

One of the biggest and well-known challenges in many biorefineries is dealing with lignin. Lignin is a major component of biomass. It is typically between 15-35 wt % (dry basis) of the biomass material. Lignin has good fuel value, similar to some types of coal.

The word lignin is derived from the Latin word "lignum" meaning wood. Lignin is a natural polymer and is an essential part of wood and other forms of cellulosic biomass, including agricultural crop residues such as sugarcane bagasse. Lignin performs multiple functions that are essential to the life of the plant, including transport of nutrition and durability of the biomass. Lignin imparts rigidity to the cell walls and acts as a binder, creating a flexible composite cellulose-hemicellulose-lignin material that is outstandingly resistant to impact, compression, and bending.

After polysaccharides (polymers of sugar), lignin is the most abundant organic polymer in the plant world. Lignin is a very complex natural polymer with many random couplings, and therefore lignin has no exact chemical structure. The molecular structure of lignin consists primarily of carbon ring structures (benzene rings with methoxyl, hydroxyl, and propyl groups.

Various processes can be used to remove and isolate lignin from biomass. Each process, however, produces material of different composition and properties. Generally there are four important factors to take into account when working with lignin:
  1. Source of the lignin.
  2. Method used to remove lignin from the biomass.
  3. Method(s) used to purify the lignin.
  4. Nature of the chemical modification of the lignin after isolation.

These factors influence the properties of the lignin. Important properties of lignin formulations include molecular weight, chemical composition, and the type and distribution of chemical functional groups.

Separation and recovery of lignin is quite difficult. It is possible to break the lignin-cellulose-hemicellulose matrix and recover the lignin through a variety of treatments on the lignocellulosic material. However, known lignin recovery methods generally have one or more important commercial-scale limitations. Lignin purification from biomass is a classic chemical-engineering problem with complex chemistries and transport phenomena, criticality of reactor design and scale-up, serious analytical challenges, and many practical issues arising from lignin's propensity to stick to equipment and piping.

Lignin can be difficult to process in biorefineries because it has a tendency to deposit on solid surfaces and cause plugging. Although lignin handling has always been known to be a challenge, there remains a need in the art for ways to either avoid lignin precipitation or to deal with it after it occurs. Other difficulties are caused by downstream fermentation inhibition caused by lignin, as well as lignin fragments and derivatives (e.g., phenolics, acids, and other compounds).

Lignin separations challenges appear to be particularly troubling problem for acidic pretreatments of biomass or biomass-derived liquors. For example, in van Heiningen et al., "Which fractionation process can overcome the techno-economic hurdles of a lignocellulosic biorefinery," Proceedings of the AIChE Annual Meeting, Minneapolis, Minn. (2011), it is cautioned that "an operating problem which has mostly been overlooked for acidic pretreatment is formation and precipitation of sticky lignin on reactor walls and piping." The lack of R&D attention to this problem is stated to be that it only "becomes apparent in continuous larger scale operation after one to two week operation."

In view of the aforementioned needs in the art, improvements are clearly needed to deal with lignin precipitation during acidic hydrolysis of biomass and/or biomass hydrolysates (such as hemicellulose-containing liquid extracts).

SUMMARY OF THE INVENTION

The present invention addresses the aforementioned needs in the art.

In some variations, the invention provides a continuous process for producing hemicellulose sugars from a biomass extraction liquor, the process comprising:
  (a) providing or obtaining a biomass extraction liquor containing water, hemicellulose oligomers, and dissolved or suspended lignin;
  (b) optionally introducing an acid catalyst to the biomass extraction liquor;
  (c) for a first period of time, feeding the biomass extraction liquor through a first hydrolysis reactor under effective hydrolysis reaction conditions to hydrolyze the hemicellulose oligomers into hemicellulose monomers;
  (d) at a first switching time, diverting the biomass extraction liquor from the first hydrolysis reactor to a second hydrolysis reactor;
  (e) for a second period of time, feeding the biomass extraction liquor through the second hydrolysis reactor under the effective hydrolysis reaction conditions;
  (f) during the second period of time, cleaning the first hydrolysis reactor by introducing a cleaning agent selected from the group consisting of steam, an alkaline solution, an organic solvent, and combinations thereof, wherein the cleaning agent is effective to dissolve precipitated lignin formed from the lignin under the effective hydrolysis reaction conditions;

(g) at a second switching time, diverting the biomass extraction liquor from the second hydrolysis reactor back to the first hydrolysis reactor or to a third hydrolysis reactor for hydrolyzing the hemicellulose oligomers into hemicellulose monomers, while concurrently cleaning the second hydrolysis reactor by introducing the cleaning agent to dissolve the precipitated lignin; and (h) repeating steps (c) to (g) a plurality of times, thereby continuously producing hemicellulose sugars from the biomass extraction liquor.

In some embodiments, the biomass extraction liquor is obtained from steam or liquid hot-water extraction of biomass. In some embodiments, the biomass extraction liquor is obtained from acidic liquid extraction of biomass. In some embodiments, the biomass extraction liquor is obtained from fractionation of biomass in the presence of water, a solvent for lignin, and an acid.

The process may employ two hydrolysis reactors, three hydrolysis reactors, or more than three hydrolysis reactors. The hydrolysis reactors may be heat exchangers, or may be integrated with heat exchangers, such as heat exchangers with indirect steam heating to reach hydrolysis temperatures.

In some embodiments, the biomass extraction liquor (either as provided or following addition of an acid catalyst) has a pH from about 0 to about 6, such as from about 1 to about 4, or about 0.5, 1.0, 1.5, 2.0, 2.5, 3.0, 3.5, 4.0, 4.5, 5.0, 5.5, or 6.0. The biomass extraction liquor provided or obtained in step (a) may contain suitable acidity for hydrolysis, in which case step (b) need not be performed. For example, suitable acidity may arise from the presence of lignosulfonic acid, acetic acid, formic acid, or other acids derived from upstream pretreatment of the starting biomass.

In some embodiments, step (b) is performed, and the acid catalyst is a sulfur-containing compound selected from the group consisting of sulfur dioxide, sulfurous acid, sulfur trioxide, sulfuric acid, sulfonic acid, lignosulfonic acid, and combinations thereof.

The effective hydrolysis reaction conditions may include an acid content from about 0.1 wt % to about 20 wt %, a temperature from about 100° C. to about 220° C., and a residence time from about 2 minutes to about 4 hours. In certain embodiments, the effective hydrolysis reaction conditions include an acid content from about 0.5 wt % to about 2 wt %, a temperature from about 120° C. to about 180° C., and a residence time from about 5 minutes to about 90 minutes. Each of the hydrolysis reactors may be operated at the same or different reaction conditions.

Depending on the starting feedstock, the hydrolysis conditions, the design of the hydrolysis reactor, and so on, a wide range of operating/switching times may be employed. In various embodiments, the first period of time and the second period of time are each independently selected from about 1 day to about 3 months.

In preferred embodiments, the cleaning agent includes steam to mechanically dislodge the precipitated lignin. The steam may also serve to heat up the precipitated lignin phase to soften the lignin, assisting in its removal.

In some embodiments, the cleaning agent includes an alkaline solution to chemically dissolve or react with the precipitated lignin, wherein the alkaline solution comprises a base selected from the group consisting of sodium hydroxide, potassium hydroxide, calcium oxide, magnesium hydroxide, ammonia, and combinations thereof.

In these or other embodiments, the cleaning agent includes an organic solvent to chemically dissolve the precipitated lignin, wherein the organic solvent comprises a compound selected from the group consisting of an aliphatic alcohol, an aromatic alcohol, a ketone, an aldehyde, and combinations thereof.

In certain embodiments of the invention, the cleaning agent includes steam to mechanically dislodge the precipitated lignin, followed by an alkaline solution to chemically dissolve or react with the precipitated lignin or with mechanically dislodged lignin. The sequence may be reversed, i.e. alkaline solution followed by steam. Or the steam and alkaline solution may be introduced at the same time.

In certain embodiments of the invention, the cleaning agent includes steam to mechanically dislodge the precipitated lignin, followed by an organic solvent to chemically dissolve the precipitated lignin or mechanically dislodged lignin. The sequence may be reversed, i.e. organic solvent followed by steam. Or the steam and organic solvent may be introduced at the same time.

In specific embodiments, the cleaning agent includes steam, an alkaline solution, and an organic solvent, introduced in any sequence.

Some variations provide a continuous process for producing hemicellulose derivatives from a biomass extraction liquor, the process comprising:

(a) providing or obtaining a biomass extraction liquor containing water, hemicellulose oligomers, and dissolved or suspended lignin;

(b) introducing an acid catalyst to the biomass extraction liquor;

(c) for a first period of time, feeding the biomass extraction liquor through a first reactor under effective reaction conditions to hydrolyze the hemicellulose oligomers into hemicellulose monomers and to convert the hemicellulose monomers into one or more hemicellulose derivatives;

(d) at a first switching time, diverting the biomass extraction liquor from the first reactor to a second reactor;

(e) for a second period of time, feeding the biomass extraction liquor through the second reactor under the effective reaction conditions;

(f) during the second period of time, cleaning the first reactor by introducing a cleaning agent selected from the group consisting of steam, an alkaline solution, an organic solvent, and combinations thereof, wherein the cleaning agent is effective to dissolve precipitated lignin formed from the lignin under the effective reaction conditions;

(g) at a second switching time, diverting the biomass extraction liquor from the second reactor back to the first reactor or to a third reactor, while concurrently cleaning the second reactor by introducing the cleaning agent to dissolve the precipitated lignin; and (h) repeating steps (c) to (g) a plurality of times, thereby continuously producing hemicellulose derivatives from the biomass extraction liquor.

The hemicellulose derivatives may be selected from the group consisting of furfural, hydroxymethylfurfural, levulinic acid, formic acid, and combinations thereof, for example.

The present invention also provides a system configured for continuously producing hemicellulose sugars and/or hemicellulose derivatives from a biomass extraction liquor, the system comprising at least a first hydrolysis reactor and a second hydrolysis reactor, wherein each of the hydrolysis reactors is in switchable communication with an operating feed stream of a biomass extraction liquor containing water, hemicellulose oligomers, and dissolved or suspended lignin, an optional operating acid catalyst feed stream, and a cleaning feed stream of a cleaning agent selected from the group consisting of steam, an alkaline solution, an organic solvent, and combinations thereof.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The present invention, in some variations, is premised on the design of a system incorporating multiple hydrolysis reactors that can be configured to enable a continuous process, overcoming the known problem that conventional hydrolysis reactors often must be shut down due to lignin deposition and scaling.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

In some variations, the invention provides a continuous process for producing hemicellulose sugars from a biomass extraction liquor, the process comprising:

(a) providing or obtaining a biomass extraction liquor containing water, hemicellulose oligomers, and dissolved or suspended lignin;

(b) optionally introducing an acid catalyst to the biomass extraction liquor;

(c) for a first period of time, feeding the biomass extraction liquor through a first hydrolysis reactor under effective hydrolysis reaction conditions to hydrolyze the hemicellulose oligomers into hemicellulose monomers;

(d) at a first switching time, diverting the biomass extraction liquor from the first hydrolysis reactor to a second hydrolysis reactor;

(e) for a second period of time, feeding the biomass extraction liquor through the second hydrolysis reactor under the effective hydrolysis reaction conditions;

(f) during the second period of time, cleaning the first hydrolysis reactor by introducing a cleaning agent selected from the group consisting of steam, an alkaline solution, an organic solvent, and combinations thereof, wherein the cleaning agent is effective to dissolve precipitated lignin formed from the lignin under the effective hydrolysis reaction conditions;

(g) at a second switching time, diverting the biomass extraction liquor from the second hydrolysis reactor back to the first hydrolysis reactor or to a third hydrolysis reactor for hydrolyzing the hemicellulose oligomers into hemicellulose monomers, while concurrently cleaning the second hydrolysis reactor by introducing the cleaning agent to dissolve the precipitated lignin; and (h) repeating steps (c) to (g) a plurality of times, thereby continuously producing hemicellulose sugars from the biomass extraction liquor.

In some embodiments, the biomass extraction liquor is obtained from steam or liquid hot-water extraction of biomass. In some embodiments, the biomass extraction liquor is obtained from acidic liquid extraction of biomass. In some embodiments, the biomass extraction liquor is obtained from fractionation of biomass in the presence of water, a solvent for lignin, and an acid. The biomass extraction liquor may contain up to 20 wt % suspended solids, for example. Suspended solids may include lignin, ash, or cellulose particles, for example.

The process may employ two hydrolysis reactors, three hydrolysis reactors, or more than three hydrolysis reactors.

The hydrolysis reactors may be heat exchangers, or may be integrated with heat exchangers, such as heat exchangers with indirect steam heating to reach hydrolysis temperatures.

In some embodiments, the biomass extraction liquor (either as provided or following addition of an acid catalyst) has a pH from about 0 to about 6, such as from about 1 to about 4, or about 0.5, 1.0, 1.5, 2.0, 2.5, 3.0, 3.5, 4.0, 4.5, 5.0, 5.5, or 6.0. The biomass extraction liquor provided or obtained in step (a) may contain suitable acidity for hydrolysis, in which case step (b) need not be performed. For example, suitable acidity may arise from the presence of lignosulfonic acid, acetic acid, formic acid, or other acids derived from upstream pretreatment of the starting biomass.

In some embodiments, step (b) is performed, and the acid catalyst is a sulfur-containing compound selected from the group consisting of sulfur dioxide, sulfurous acid, sulfur trioxide, sulfuric acid, sulfonic acid, lignosulfonic acid, and combinations thereof.

The effective hydrolysis reaction conditions may include an acid content from about 0.1 wt % to about 20 wt %, a temperature from about 100° C. to about 220° C., and a residence time from about 2 minutes to about 4 hours. In certain embodiments, the effective hydrolysis reaction conditions include an acid content from about 0.5 wt % to about 2 wt %, a temperature from about 120° C. to about 180° C., and a residence time from about 5 minutes to about 90 minutes. Each of the hydrolysis reactors may be operated at the same or different reaction conditions.

Effective extraction conditions may include contacting the lignocellulosic biomass with steam (at various pressures in saturated, superheated, or supersaturated form) and/or hot water. The hydrolysis catalyst may be an acid catalyst, a base catalyst, or an enzymatic catalyst. Preferably, the hydrolysis catalyst is an acid catalyst such as one selected from the group consisting of sulfuric acid, sulfurous acid, sulfur dioxide, and combinations thereof. In some embodiments, the process is a variation of the Green Power+® process technology which is commonly owned with the assignee of this patent application.

The hemicellulose sugars may be recovered and fermented to a fermentation product (e.g., ethanol, butanol, or lactic acid), recovered and purified as a sugar product, or chemically converted to a hemicellulose derivative (e.g., furfural), for example.

In some embodiments, the fermentable hemicellulose sugars are recovered from solution, in purified form. In some embodiments, the fermentable hemicellulose sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Depending on the starting feedstock, the hydrolysis conditions, the design of the hydrolysis reactor, and so on, a wide range of operating/switching times may be employed. In various embodiments, the first period of time and the second period of time are each independently selected from about 1 day to about 3 months, such as about 2, 3, 4, 5, 6 days or about 1, 2, 3, 4 weeks or about 1, 2, 3 months or more. It is also possible to apply the principles of the invention to a system in which operating times are relatively short, such as 16, 12, 8, or 4 hours, before switching to cleaning mode.

In preferred embodiments, the cleaning agent includes steam to mechanically dislodge the precipitated lignin. The steam may also serve to heat up the precipitated lignin phase to soften the lignin, or potentially chemically modify it, thereby assisting in its removal.

In some embodiments, the cleaning agent includes an alkaline solution to chemically dissolve or react with the precipitated lignin, wherein the alkaline solution comprises a base selected from the group consisting of sodium hydroxide, potassium hydroxide, calcium oxide, magnesium hydroxide, ammonia, and combinations thereof.

In these or other embodiments, the cleaning agent includes an organic solvent to chemically dissolve the precipitated lignin, wherein the organic solvent comprises a compound selected from the group consisting of an aliphatic alcohol (e.g., ethanol), an aromatic alcohol, a ketone (e.g., acetone), an aldehyde, and combinations thereof.

In certain embodiments of the invention, the cleaning agent includes steam to mechanically dislodge the precipitated lignin, followed by an alkaline solution to chemically dissolve or react with the precipitated lignin or with mechanically dislodged lignin. The sequence may be reversed, i.e. alkaline solution followed by steam. Or the steam and alkaline solution may be introduced at the same time.

In certain embodiments of the invention, the cleaning agent includes steam to mechanically dislodge the precipitated lignin, followed by an organic solvent to chemically dissolve the precipitated lignin or mechanically dislodged lignin. The sequence may be reversed, i.e. organic solvent followed by steam. Or the steam and organic solvent may be introduced at the same time.

In specific embodiments, the cleaning agent includes steam, an alkaline solution, and an organic solvent, introduced in any sequence. The alkaline solution will generally also contain water, and the organic solvent may contain water. The steam may also contain an organic solvent, an acid, a base, or another additive.

The lignin that is removed from the system during cleaning may be recovered for combustion (energy production) or for other uses. Following separation of lignin, the cleaning agent may then be reused in another cleaning cycle.

The starting biomass feedstock may be selected from hardwoods, softwoods, forest residues, agricultural residues (such as sugarcane bagasse), industrial wastes, consumer wastes, or combinations thereof.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse.

Some variations provide a continuous process for producing hemicellulose derivatives from a biomass extraction liquor, the process comprising:

(a) providing or obtaining a biomass extraction liquor containing water, hemicellulose oligomers, and dissolved or suspended lignin;

(b) introducing an acid catalyst to the biomass extraction liquor;

(c) for a first period of time, feeding the biomass extraction liquor through a first reactor under effective reaction conditions to hydrolyze the hemicellulose oligomers into hemicellulose monomers and to convert the hemicellulose monomers into one or more hemicellulose derivatives;

(d) at a first switching time, diverting the biomass extraction liquor from the first reactor to a second reactor;

(e) for a second period of time, feeding the biomass extraction liquor through the second reactor under the effective reaction conditions;

(f) during the second period of time, cleaning the first reactor by introducing a cleaning agent selected from the group consisting of steam, an alkaline solution, an organic solvent, and combinations thereof, wherein the cleaning agent is effective to dissolve precipitated lignin formed from the lignin under the effective reaction conditions;

(g) at a second switching time, diverting the biomass extraction liquor from the second reactor back to the first reactor or to a third reactor, while concurrently cleaning the second reactor by introducing the cleaning agent to dissolve the precipitated lignin; and (h) repeating steps (c) to (g) a plurality of times, thereby continuously producing hemicellulose derivatives from the biomass extraction liquor.

The hemicellulose derivatives may be selected from the group consisting of furfural, hydroxymethylfurfural, levulinic acid, formic acid, and combinations thereof, for example.

The present invention also provides a system configured for continuously producing hemicellulose sugars and/or hemicellulose derivatives from a biomass extraction liquor, the system comprising at least a first hydrolysis reactor and a second hydrolysis reactor, wherein each of the hydrolysis reactors is in switchable communication with an operating feed stream of a biomass extraction liquor containing water, hemicellulose oligomers, and dissolved or suspended lignin, an optional operating acid catalyst feed stream, and a cleaning feed stream of a cleaning agent selected from the group consisting of steam, an alkaline solution, an organic solvent, and combinations thereof. Such a system is depicted in FIG. 1, which is a process-flow diagram of a continuous hydrolysis and cleaning system.

Figure 1:
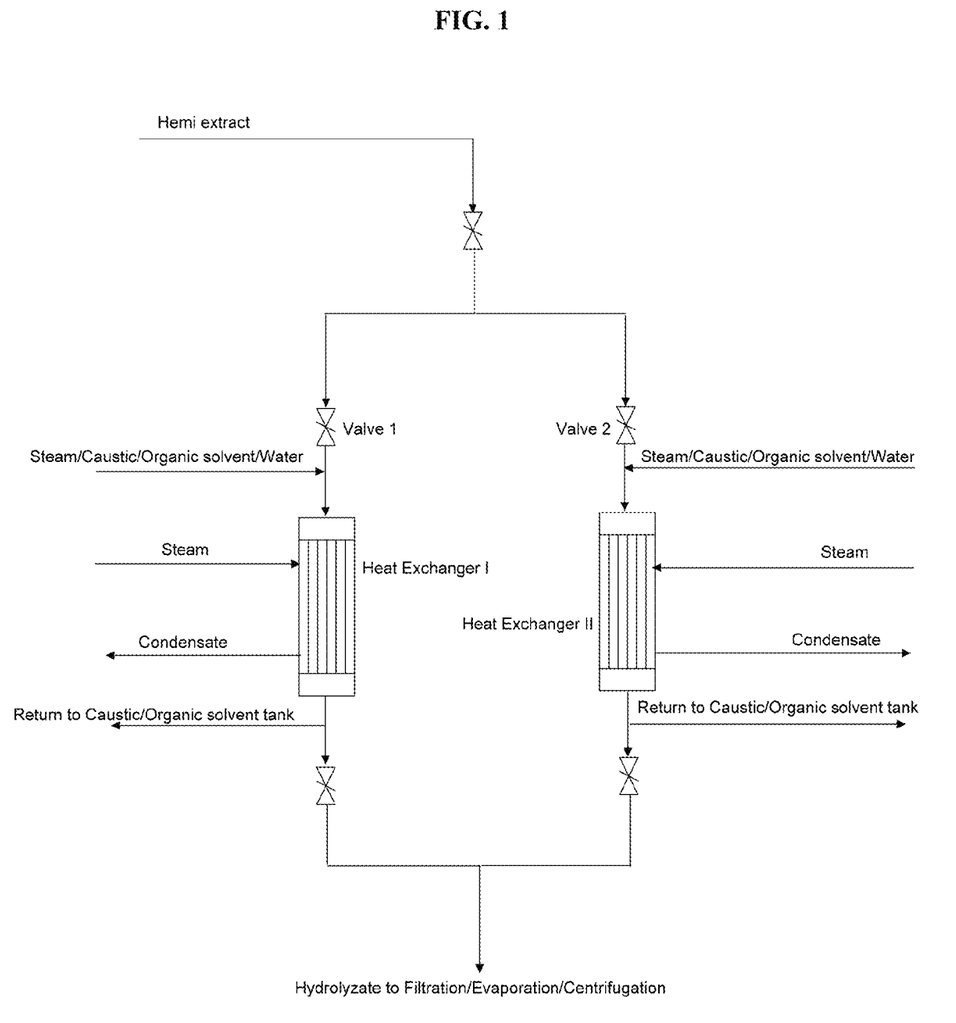
FIG. 1 is a simplified process-flow diagram depicting the process of some embodiments of the present invention.

With reference to FIG. 1, which is an exemplary continuous process of acid hydrolysis with cleaning system. A hemicellulose-containing extract generated from lignocellulosic biomass with or without the addition of an acid is transferred to heat exchanger I, valve 2 is closed and heat exchanger II is in the mode of idle or cleaning. The hemicellulose-containing extract is heated to the target temperature with steam and treated for the desired residence time by controlling the flow rate. After heat exchanger I runs for the desired time, valve 1 is closed and valve 2 is opened. The lignin precipitate and scaling reduces the heat-transfer efficiency in heat exchanger I. The hemicellulose-containing extract is therefore transferred to (clean) heat exchanger II for hydrolysis.

Figure 2:
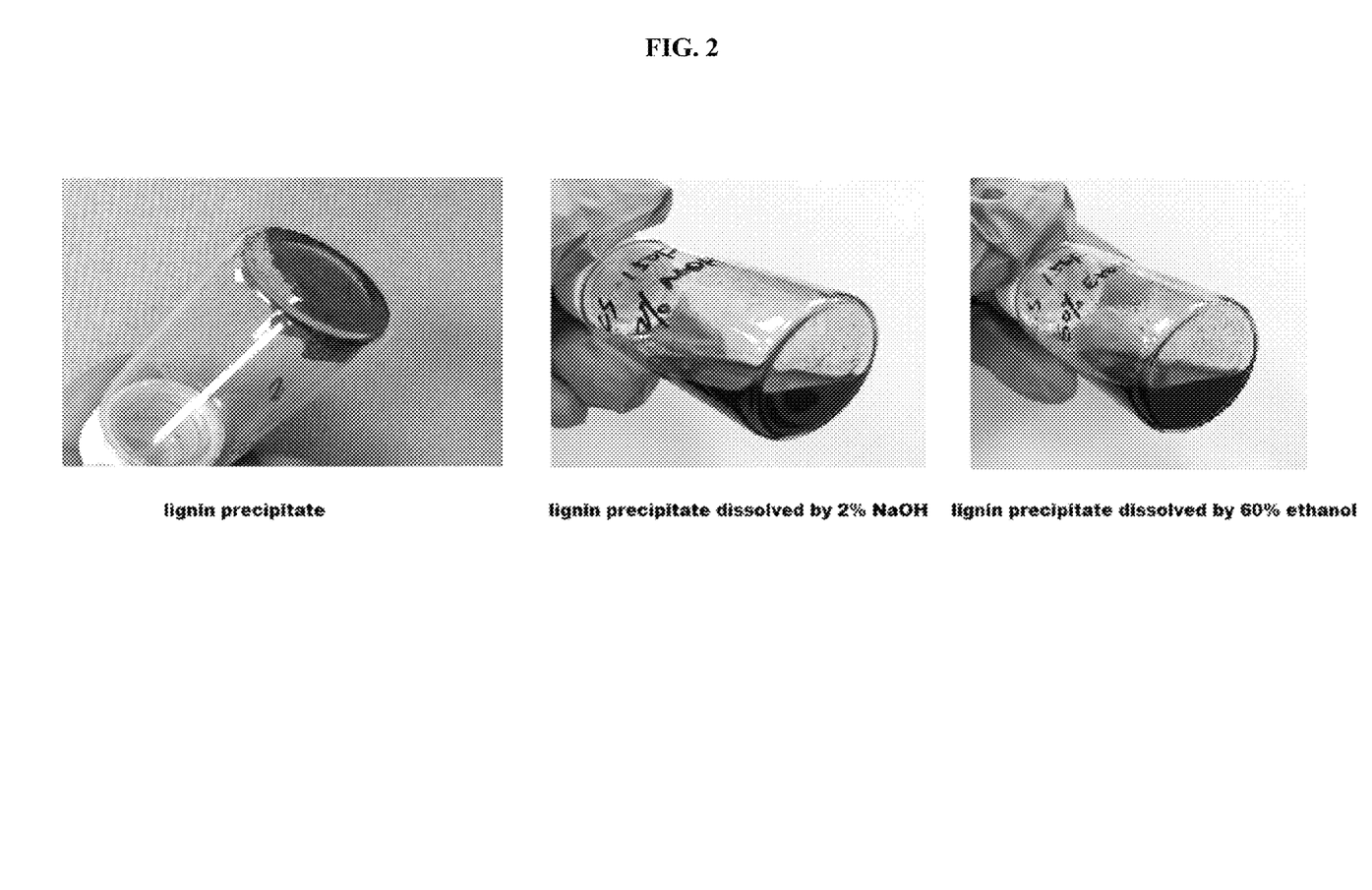
FIG. 2 is a series of photographs illustrating that certain lignin precipitates can be dissolved by alkaline solution as well as by organic solvent.

For cleaning, in some embodiments, first high-pressure steam impels the residue derived from the hemicellulose-containing extract in heat exchanger I. Second, an alkaline solution (e.g., caustic soda, NaOH) is pumped through the heat exchanger to dissolve the lignin precipitate on the walls. Alternatively, or additionally, the heat exchanger is cleaned with an organic solvent, for example ethanol or acetone. As depicted in FIG. 2, lignin precipitate can be dissolved by caustic solution as well as by organic solvent. Finally, the heat exchanger is rinsed with water. The two heat exchangers run alternatively in hydrolysis and cleaning modes. Therefore, this system is able to hydrolyze the hemicellulose-containing extract continuously.

Figure 3:
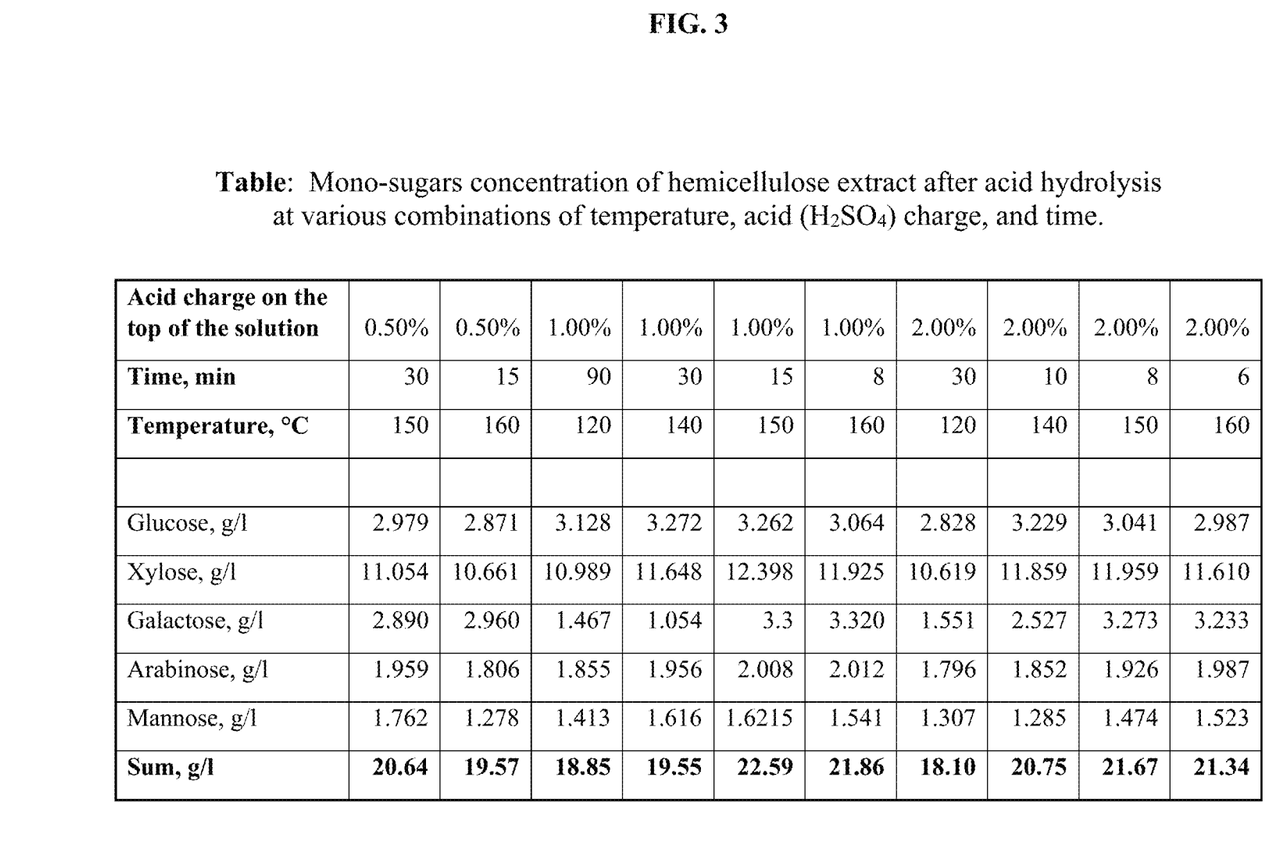
FIG. 3 is a table of experimental monosugar concentrations after acid hydrolysis of a hemicellulose-containing extract at various temperatures, acid charges, and residence times.

The table in FIG. 3 presents experimental results of monosugar concentrations after acid hydrolysis of a hemicellulose-containing extract at various temperatures, acid charges, and residence times. The solids content of this hemicellulose-containing extract is 4.2 wt % and the maximum monosugar concentration after acid hydrolysis is approximately 20 g/l. From the table, preferred conditions to obtain a maximum monosugar yield include 0.50% acid charge, 15 minutes, 160° C.; 1.0% acid charge, 15 minutes, 150° C.; and 1.0% acid charge, 8 minutes, 160° C.

This system can also be used for the generation of hydroxymethylfurfural (HMF), furfural, levulinic acid, and/or formic acid by adjusting the conditions of acid charge, temperature, and/or residence time. HMF may be formed from hexoses in the extract, while furfural may be formed from pentoses in the extract. Severe reaction conditions can further degrade HMF to levulinic acid and formic acid, as is known.

Therefore, variations of this invention may continuously convert hemicellulose-containing extracts (up to 20 wt % or higher solids content) to generate monosugars, acetic acid, HMF, furfural, levulinic acid, and/or formic acid by adjusting conditions of acid charge (e.g., 0-20 wt %), temperature (e.g., 100-220° C.) and residence time (e.g., 1-240 minutes). Higher temperatures (such as 180-220° C.) are typically beneficial when hemicellulose derivatives are desired.

Note that in this disclosure, "precipitated lignin" includes not only chemically condensed lignin but also suspended lignin that physically scales or clogs pipes, pumps, reactor walls, etc. The lignin may be in a solid phase, or in the form of a slurry or suspension.

All references to "lignin" herein shall not be construed as limiting to any particular type of lignin or process to produce lignin. For example, in some embodiments, lignin refers to "Hydrolysis Lignin," a water-insoluble product produced by the strong acid hydrolysis of woody material to produce sugars. The resulting lignin is altered structurally and contains sugar degradation products, wood extractives, and inorganic compounds.

In various embodiments, lignin refers to Brauns Lignin (obtained by the solvent extraction of wood meal); Cellulolytic Enzyme Lignin (isolated by cellulolytic enzyme treatment of finely ground wood meal followed by solvent extraction); Dioxane Acidolysis Lignin (isolated by the treatment of woody material with dioxane/dilute HCl); Milled Wood Lignin (isolated by solvent extraction and purification of finely ground wood meal; also known as Bjorkman Lignin); Klason Lignin (isolated through the strong acid degradation of woody materials); Periodate Lignin (isolated through successive treatments of woody material with sodium periodate followed by boiling water); Kraft Lignin (generated through Kraft pulping, wherein water-insoluble lignin is made from woody material in reaction with NaOH and $Na_2S$ at temperatures of 155-175° C.; Lignosulfonates from Acid Sulfite Pulping (water-soluble lignin obtained by reacting woody material with sulfur dioxide and a metal bisulfite at pH 1-2 and a temperature between 125-145° C.); Lignosulfonates from Bisulfite Pulping (water-soluble lignin obtained by reacting woody material with a metal bisulfite salt at a pH of 3-5 at 150-175° C.; Lignosulfonates from Neutral Sulfite Semi Chemical Process (water-soluble lignin obtained by reacting woody material with salts of bisulfite/sulfite at pH 6-9 prior to mechanical refining; Lignosulfonates from Alkaline Sulfite—Anthraquinone Pulping (water-soluble lignin obtained by reacting woody material with sodium sulfite and a catalytic amount of anthraquinone at pH 9-13 and 160-

180° C.); Organosolv Lignin (water-insoluble lignin or water-soluble sulfonated lignin obtained from an organic solvent-based system); and Steam Explosion Lignin (water-insoluble lignin obtained by separating woody material into fibers through high temperature/high pressure treatment with steam.

In addition, the invention principles also apply to char, humins, or other degradation products which can sometimes be similar in composition, structure, or properties, compared to lignin. For instance, in some embodiments, hemicellulose oligomers are converted to furfural which is then degraded to humins or other resins.

The lignin may be separated from the cleaning solution using a variety of separation devices. The separation unit may be selected from filters, membranes, decanters, clarifiers, centrifuges, decanting centrifuges, cyclones, hydrocyclones, precipitators, electrostatic precipitators, evaporators, flash vessels, distillation columns, and so on. The lignin may be recovered in solid form, in slurry form, or as a solution in liquid.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A continuous process for producing hemicellulose sugars from a biomass extraction liquor, said process comprising:
   (a) providing or obtaining a biomass extraction liquor containing water, hemicellulose oligomers, and dissolved or suspended lignin;
   (b) optionally introducing an acid catalyst to said biomass extraction liquor;
   (c) for a first period of time, feeding said biomass extraction liquor through a first hydrolysis reactor under effective hydrolysis reaction conditions to hydrolyze said hemicellulose oligomers into hemicellulose monomers;
   (d) at a first switching time, diverting said biomass extraction liquor from said first hydrolysis reactor to a second hydrolysis reactor;
   (e) for a second period of time, feeding said biomass extraction liquor through said second hydrolysis reactor under said effective hydrolysis reaction conditions;
   (f) during said second period of time, cleaning said first hydrolysis reactor by introducing a cleaning agent selected from the group consisting of steam, an alkaline solution, an organic solvent, and combinations thereof, wherein said cleaning agent is effective to dissolve precipitated lignin formed from said lignin under said effective hydrolysis reaction conditions;
   (g) at a second switching time, diverting said biomass extraction liquor from said second hydrolysis reactor back to said first hydrolysis reactor or to a third hydrolysis reactor for hydrolyzing said hemicellulose oligomers into hemicellulose monomers, while concurrently cleaning said second hydrolysis reactor by introducing said cleaning agent to dissolve said precipitated lignin; and
   (h) repeating steps (c) to (g) a plurality of times, thereby continuously producing hemicellulose sugars from said biomass extraction liquor.

2. The process of claim 1, wherein said biomass extraction liquor is obtained from steam or liquid hot-water extraction of biomass.

3. The process of claim 1, wherein said biomass extraction liquor is obtained from acidic liquid extraction of biomass.

4. The process of claim 1, wherein said biomass extraction liquor is obtained from fractionation of biomass in the presence of water, a solvent for lignin, and an acid.

5. The process of claim 1, wherein said process employs two hydrolysis reactors consisting of said first hydrolysis reactor and said second hydrolysis reactor.

6. The process of claim 1, wherein said process employs three or more hydrolysis reactors comprising said first hydrolysis reactor, said second hydrolysis reactor, and said third hydrolysis reactor.

7. The process of claim 1, wherein each of said hydrolysis reactors is, or is integrated with, a heat exchanger with indirect steam heating.

8. The process of claim 1, wherein said biomass extraction liquor has a pH from about 0 to about 6.

9. The process of claim 8, wherein said biomass extraction liquor has a pH from about 1 to about 4.

10. The process of claim 1, wherein said biomass extraction liquor provided or obtained in step (a) contains suitable acidity for hydrolysis, and wherein step (b) is not performed.

11. The process of claim 10, wherein said suitable acidity arises from the presence of lignosulfonic acid.

12. The process of claim 1, wherein step (b) is performed, and wherein said acid catalyst is a sulfur-containing compound selected from the group consisting of sulfur dioxide, sulfurous acid, sulfur trioxide, sulfuric acid, sulfonic acid, lignosulfonic acid, and combinations thereof.

13. The process of claim 1, wherein said effective hydrolysis reaction conditions include an acid content from about 0.1 wt % to about 20 wt %, a temperature from about 100° C. to about 220° C., and a residence time from about 2 minutes to about 4 hours.

14. The process of claim 13, wherein said effective hydrolysis reaction conditions include an acid content from about 0.5 wt % to about 2 wt %, a temperature from about 120° C. to about 180° C., and a residence time from about 5 minutes to about 90 minutes.

15. The process of claim 1, wherein each of said hydrolysis reactors is operated at the same reaction conditions.

16. The process of claim 1, wherein said first period of time and said second period of time are each independently selected from about 1 day to about 3 months.

17. The process of claim 1, wherein said cleaning agent includes said steam to mechanically dislodge said precipitated lignin.

18. The process of claim 1, wherein said cleaning agent includes said alkaline solution to chemically dissolve or react with said precipitated lignin, wherein said alkaline solution comprises a base selected from the group consisting of sodium hydroxide, potassium hydroxide, calcium oxide, magnesium hydroxide, ammonia, and combinations thereof.

19. The process of claim 1, wherein said cleaning agent includes said organic solvent to chemically dissolve said precipitated lignin, wherein said organic solvent comprises a compound selected from the group consisting of an aliphatic alcohol, an aromatic alcohol, a ketone, an aldehyde, and combinations thereof.

20. The process of claim 1, wherein said cleaning agent includes said steam to mechanically dislodge said precipitated lignin, followed by said alkaline solution to chemically dissolve or react with said precipitated lignin or with mechanically dislodged lignin.

21. The process of claim 1, wherein said cleaning agent includes said steam to mechanically dislodge said precipitated lignin, followed by said organic solvent to chemically dissolve said precipitated lignin or mechanically dislodged lignin.

22. The process of claim 1, wherein said cleaning agent includes steam, said alkaline solution, and said organic solvent, introduced in any sequence.

* * * * *